(12) United States Patent
Sato et al.

(10) Patent No.: US 6,568,281 B1
(45) Date of Patent: May 27, 2003

(54) ULTRASONIC-WAVE PROPAGATION-TIME MEASURING METHOD, GAS-PRESSURE MEASURING METHOD, GAS-FLOW RATE MEASURING METHOD, AND GAS SENSOR

(75) Inventors: Yoshikuni Sato, Aichi (JP); Keigo Banno, Aichi (JP); Hideki Ishikawa, Aichi (JP); Noboru Ishida, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/635,897

(22) Filed: Aug. 11, 2000

(30) Foreign Application Priority Data

Aug. 16, 1999 (JP) ............................................. 11-229776
Jun. 21, 2000 (JP) ....................................... 2000-186379

(51) Int. Cl.$^7$ ................................................. G01F 1/66
(52) U.S. Cl. ............................. 73/861.27; 73/861.28; 73/861.29
(58) Field of Search .................... 73/861.25–861.29

(56) References Cited

U.S. PATENT DOCUMENTS

| | | | |
|---|---|---|---|
| 4,003,256 A | * | 1/1977 | Donelan et al. .......... 73/861.27 |
| 4,515,021 A | | 5/1985 | Wallace et al. |
| 4,538,469 A | | 9/1985 | Lynnworth et al. |
| 4,754,650 A | * | 7/1988 | Smalling et al. .......... 73/861.28 |
| 5,277,070 A | * | 1/1994 | Dorr ........................ 73/861.27 |
| 5,533,408 A | * | 7/1996 | Oldenziel et al. ........ 73/861.06 |
| 5,625,140 A | * | 4/1997 | Cadet et al. ............... 73/24.01 |
| 6,116,080 A | * | 9/2000 | Logue et al. .............. 73/24.05 |

FOREIGN PATENT DOCUMENTS

| | | |
|---|---|---|
| JP | 60-502171 | 12/1985 |
| JP | 5-72527 | 10/1993 |

OTHER PUBLICATIONS

Myrna C. Sultan et al., "Closed Loop Canister Purge Control Systems," SAE Technical Paper Series 980206, Feb. 23–26, 1998, pp. 1–8.

* cited by examiner

Primary Examiner—Hezron Williams
Assistant Examiner—Lilybett Martir
(74) Attorney, Agent, or Firm—Sughrue Mion, PLLC

(57) ABSTRACT

An ultrasonic-wave propagation time measuring method which enables determination of accurate propagation time, a gas-pressure measuring method, a gas-flow-rate measuring method, and a gas sensor. A reception wave which has been transmitted and received by an ultrasonic element 5 is shaped and integrated by an integration circuit 67 to obtain an integral value. A peak value of the integral value is held by a peak-hold circuit 39. As to detection of gas concentration, a resistance-voltage-division circuit 41 sets a reference value on the basis of the peak value, and a point in time when the integral value of the reception wave is judged by a comparator 43 to have reached the reference value is regarded as an arrival time. Subsequently, a gas concentration is detected on the basis of a period between the emission time and the arrival time. As to detection of gas pressure and flow rate, the gas pressure is detected on the basis of the peak value, and further, the gas flow rate is calculated on the basis of the gas pressure.

6 Claims, 14 Drawing Sheets

ULTRASONIC-WAVE PROPAGATION-TIME MEASURING METHOD, GAS-PRESSURE MEASURING METHOD, GAS-FLOW RATE MEASURING METHOD, AND GAS SENSOR

BACKGROUND OF THE INVENTION

1. Field of the Invention

The present invention relates to an ultrasonic-wave propagation-time measuring method, a gas-pressure measuring method, a gas-flow-rate measuring method, and a gas sensor.

2. Description of the Related Art

Techniques for measuring sound velocity on the basis of propagation time of ultrasonic waves have been proposed in, for example, Japanese Patent Publication (kokoku) No. 5-72527 and Japanese Patent Application Laid-Open No. 60-502171.

In these techniques, an ultrasonic element is caused to transmit an ultrasonic wave (transmission wave) and receive its reflection wave (reception wave); and sound velocity is measured on the basis of the propagation time between transmission of the transmission wave and reception of the reception wave.

In a well-known method of measuring propagation time; more particularly, with regard to detecting the reception signal, a threshold level (reference value) of a comparator is fixed, and the reception wave itself or an integrated value of the reception wave is compared with the fixed threshold level.

However, ultrasonic reception waves sometimes attenuate due to pressure or other causes. In such a case, since the conventional techniques use a fixed value for the threshold level of the comparator, a measured propagation time includes an error stemming from attenuation of the reception wave.

Thus, in some cases a sound velocity calculated from the propagation time becomes inaccurate. Therefore, a gas concentration sensor which detects gas concentration on the basis of sound velocity encounters difficulty in accurately detecting gas concentration.

SUMMARY OF THE INVENTION

The present invention has been achieved in order to solve the above problems, and an object of the invention is to provide an ultrasonic-wave propagation-time measuring method which enables accurate determination of propagation time, a gas-pressure measuring method, a gas-flow-rate measuring method, and a gas sensor.

The above objectives of the invention are achieved by providing:

(1) An ultrasonic-wave propagation-time measuring method in which an ultrasonic wave is transmitted by use of an ultrasonic element, a reflection wave of the transmission wave is received as a reception wave by use of the same ultrasonic element or a different ultrasonic element, and a period of time between transmission of the ultrasonic wave and reception of the reception wave is measured as a propagation time, the method being characterized by comprising: a reference-value setting step of integrating a reception wave or a portion thereof in order to obtain an integral value, and setting a reference value on the basis of the integrated value; and a time measurement step performed when a propagation time is to be measured and comprising integrating a reception wave or a portion thereof in order to obtain an integral value, and measuring, as an arrival time of the reception wave, a point in time when the integral value attains the reference value.

In the present invention, an ultrasonic reception wave or a portion thereof is integrated in order to obtain an integral value, and a reference value (a threshold level) is set on the basis of the integrated value. At the time of actual measurement of propagation time, a reception wave or a portion thereof is integrated in order to obtain an integral value, and a point in time when the integral value attains the reference value is measured as an arrival time of the reception wave.

That is, ultrasonic reception waves sometimes attenuate due to the surrounding atmosphere (e.g., atmospheric pressure). In such a case, when a fixed reference value is used as in the conventional techniques, the time at which an integral value of a reception wave attains the reference value varies depending on the surrounding atmosphere, so that accurate measurement of propagation time becomes impossible. Therefore, in the present invention, the reference value is adjustably set on the basis of an actual integral value.

Accordingly, when the integral value of a reception wave decreases due to attenuation of the reception wave, the reference value (which is set on the basis of the integral value) also decreases. Therefore, at the time of actual measurement, the point in time when the integral value of a reception wave attains the (lowered) reference value represents an accurate arrival time. In other words, in the present invention, the reference value itself can be adjusted in consideration of pressure and other factors which influential propagation time. Therefore, even when a reception wave is attenuated due to pressure or other causes during actual measurement, the propagation time between transmission of the transmission wave and reception of the reception wave does not change, so that accurate measurement of propagation time can be effected at all times.

(2) The ultrasonic-wave propagation-time measuring method as described in (1), which further comprises integrating the reception wave or a portion thereof in the reference-value setting step, and setting a predetermined integral value obtained during a period between the start of integration and the time when a maximum integral value is obtained as the reference value.

In embodiment (2), a reference value which is optimal for measurement of propagation time can be set freely within the range in which the integral value of the reception wave varies. For example, in order to set the reference value, a peak integral value (voltage value) which is held using a peak-hold circuit is divided by use of a resistance-voltage-division circuit.

(3) The ultrasonic-wave propagation-time measuring method as described in (2), which further comprises setting the reference value to half the maximum integral value.

In embodiment (3) above, a value corresponding to half the maximum integral value (a center point of the range of variation of the integral value) is used as the reference value. Since the reference value corresponds to the center of the range of variation of the integral value, measurement of propagation time is hardly affected by noise and other causes, and failure to judge arrival time accurately can be avoided. Therefore, the present invention is practically useful.

(4) The ultrasonic-wave propagation-time measuring method as described in (1), which comprises representing the integral value in the form of a voltage valve in the reference-value setting step, and setting a ratio of the reference value to a maximum integral value on the basis of a maximum voltage value, which represents the maximum integral value.

In embodiment (4) above, for example, a peak integral value (maximum voltage value) which is held by use of a peak-hold circuit is reduced at a predetermined ratio by use of a voltage amplifying circuit in order to set the reference value.

(5) An ultrasonic-wave propagation-time measuring method in which an ultrasonic wave is transmitted by use of an ultrasonic element, a reflection wave of the transmission wave is received as a reception wave by use of the same ultrasonic element or a different ultrasonic element, and a period of time between transmission of the ultrasonic wave and reception of the reception wave is measured as a propagation time, the method being characterized by comprising: a reference-value setting step of integrating a reception wave or a portion thereof in order to obtain an integral value, and setting a reference value on the basis of the integrated value; and a time measurement step performed when a propagation time is to be measured and measuring, as an arrival time of the reception wave, a point in time when the level of a reception wave attains the reference value.

In embodiment (5), an ultrasonic reception wave or a portion thereof is integrated in order to obtain an integral value, and a reference value is set on the basis of the integrated value. At the time of actual measurement of propagation time, the point in time when the level of a reception wave attains the reference value is measured as an arrival time of the reception wave.

As described in relation to (1) above, ultrasonic reception waves sometimes are attenuated due to atmospheric pressure and other causes. Therefore, in embodiment (5), the reference value is adjustably set on the basis of an actual integral value. In particular, in embodiment (5), at the time of actual measurement, in place of an integral value of a reception wave, the reception wave itself is used for measurement of arrival time of the reception wave.

Like (1) above, embodiment (5) enables accurate measurement of propagation time. In addition, since a reception wave itself is used at the time of actual measurement, calculation and other processing performed during the measurement can be simplified.

(6) A gas sensor which detects the concentration of a specific gas in a gas under measurement by use of the ultrasonic-wave propagation-time measuring method according to any one of (1) to (5).

Propagation time of an ultrasonic wave varies depending on the concentration of a specific gas (to be detected), such as fuel vapor, contained in a gas under measurement, such as atmospheric air. Therefore, the concentration of a specific gas can be detected through measurement of propagation time of ultrasonic waves.

In particular, in embodiment (6), since propagation time can be measured accurately by use of the above-described ultrasonic-wave propagation-time measurement method, gas concentration can be detected accurately.

The expression "integrating a portion of a reception wave" means integration of a portion (e.g., a portion useful for measurement) of a reception wave, not the entirety of the reception wave. Such integration provides the same effect as that obtained when the entirety of the reception wave is integrated. In some cases, integration of a portion of a reception wave is preferable, from the viewpoint of eliminating noise and decreasing the number of calculations.

(7) A gas-pressure measurement method comprising: transmitting an ultrasonic wave by use of an ultrasonic element; receiving a reflection wave of the transmission wave as a reception wave, by use of the same ultrasonic element or a different ultrasonic element; integrating a reception wave or a portion thereof in order to obtain an integral value; and determining the pressure of a gas under measurement on the basis of the integrated value.

In embodiment (7) above, the pressure of a gas under measurement is determined on the basis of the strength of an ultrasonic reception wave, making use of the relation between the strength of an ultrasonic reception wave and the pressure of a gas under measurement.

That is, when an ultrasonic wave propagates in a gas under measurement, the ultrasonic wave is attenuated to a greater degree as the pressure of the gas under measurement decreases, with the result that the strength of a reception wave becomes weak. Therefore, when an ultrasonic wave of constant strength is transmitted and the strength of a reception wave or a portion thereof having propagated through the gas under measurement is measured, the pressure of the gas under measurement can be measured on the basis of the strength.

In particular, in embodiment (7), a value obtained by integrating a reception wave or a portion thereof with respect to time is used as a parameter which represents the strength of the reception wave or a portion thereof. Use of such an integral value enables accurate measurement of the strength of the reception wave or a portion thereof, while eliminating influence of, for example, noise.

The following specific method may be used for calculating gas pressure from the above-mentioned integral value.

A map which represents the relationship between the integral value and pressure of the gas under measurement is prepared in advance, and the pressure of the gas under measurement is calculated using the map and an integral value obtained during actual measurement.

Unlike a method which utilizes a conventionally-employed diaphragm-type gas-pressure sensor, the gas-pressure measurement method according to the present invention does not require a mechanically-movable member. Therefore, the gas-pressure measurement method according to embodiment (7) is excellent in terms of durability and reliability of an apparatus.

(8) A gas-pressure measurement method comprising: transmitting an ultrasonic wave by use of an ultrasonic element; receiving a reflection wave of the transmission wave as a reception wave by use of the same ultrasonic element or a different ultrasonic element; and measuring the pressure of a gas under measurement on the basis of the maximum amplitude of the reception wave or a portion thereof.

As in embodiment (7), embodiment (8) provides a method of measuring the pressure of a gas under measurement while utilizing the strength of an ultrasonic reception wave. In particular, in embodiment (8), the maximum amplitude of a reception wave or a portion thereof is used as a parameter which represents the strength of the reception wave.

That is, as in the case of the integral value used in embodiment (7), the maximum amplitude is one parameter which indicates the strength of a reception wave and is a value which varies depending on the pressure of a gas under measurement. Therefore, the maximum amplitude can be used for gas-pressure measurement. For example, when the pressure of a gas under measurement is low, the maximum amplitude decreases.

Accordingly, as in the case of embodiment (7), embodiment (8) enables measurement of the pressure of a gas under measurement. In particular, in the present invention, the number of calculations during measurement can be reduced, because a process for integrating a reception wave is unnecessary.

(9) A gas-flow-rate measurement method which comprises: measuring the pressure of a gas under measurement by use of the gas-pressure measurement method described in (7) or (8); and measuring the flow rate of the gas under measurement on the basis of the measured pressure.

Embodiment (9) utilizes the phenomenon that the flow rate of a gas under measurement flowing through a flow path of a constant shape depends on a differential pressure produced in the flow path, and in the method of embodiment (9), a differential pressure produced in the flow path is first measured, and subsequently a gas flow rate is calculated on the basis of the differential pressure.

In order to measure the differential pressure in the flow path, a gas pressure at a predetermined location within the flow path is measured by use of the gas-pressure measurement method described in (7) or (8), and the differential pressure is obtained from the gas pressure.

In the case in which the gas pressure at the predetermined location in the flow path is constant (e.g., in the case in which one end of the flow path is exposed to the atmospheric pressure), the differential pressure in the flow path is univocally determined through measurement of the gas pressure at another point in the flow path. Therefore, measurement of gas pressure is required at only a single location.

Subsequently, the flow rate of the gas under measurement is calculated on the basis of the differential pressure obtained in the above-described manner.

Specifically, a map which represents the relationship between differential pressure produced in the flow path and flow rate of the gas under measurement is prepared in advance, and a flow rate of the gas under measurement is calculated using the map and an actually measured differential pressure.

In embodiment (9), since the pressure of a gas under measurement is measured, and the flow rate of the gas under measurement is calculated on the basis of the pressure, both the pressure and flow rate of the gas under measurement can be measured.

Therefore, when the pressure and flow rate of a gas under measurement are measured by use of embodiment (9), both the pressure and flow rate can be measured by use of a single gas sensor, so that cost and installation space of the gas sensor can be decreased.

(10) A gas sensor which comprises means for detecting the pressure of a gas under measurement using the gas-pressure measurement method described in (7) or (8).

The gas sensor of embodiment (10) provides effects similar to those described in relation to (7) and (8).

(11) A gas sensor which comprises means for detecting the concentration of a specific gas contained in a gas under measurement, by use of the ultrasonic-wave propagation-time measurement method described in any one of (1) to (5), and which comprises means for detecting the pressure of the gas under measurement by use of the gas-pressure measurement method described in (7) or (8).

Since the gas sensor of embodiment (11) measures the concentration of a gas under measurement in a manner similar to that used for the gas sensor described in (6), the gas sensor of embodiment (11) provides effects similar to those provided by the gas sensor described in (6).

Since the gas sensor of embodiment (11) measures the pressure of a gas under measurement in a manner similar to that used for the gas sensor described in (10), the gas sensor of embodiment (11) provides effects similar to those described in relation to (10).

Moreover, since embodiment (11) enables measurement of the concentration of a specific gas contained in a gas under measurement and the pressure of the gas under measurement by using a single gas sensor, cost and installation space of the gas sensor can be decreased as compared with the case in which gas concentration and gas pressure are measured by using different gas sensors.

Furthermore, the gas sensor of embodiment (11) measures gas concentration and gas pressure through utilization of attributes (propagation speed in measurement of concentration of a specific gas, and strength of a reception wave in pressure measurement) of ultrasonic waves propagating through the gas under measurement.

Accordingly, among structural portions of the gas sensor of embodiment (11), portions related to ultrasonic waves (e.g., an ultrasonic element, an ultrasonic propagation path, a reflection surface, and a signal processing circuit) can be used in common for gas-concentration measurement and gas-pressure measurement. Therefore, the gas sensor of embodiment (11) can be rendered further compact.

(12) A gas sensor which comprises means for detecting the pressure of a gas under measurement by use of the gas-pressure measurement method described in (7) or (8), and which comprises means for detecting the flow rate of the gas under measurement by use of the gas-flow-rate measurement method described in (9).

Since the gas sensor of embodiment (12) measures the concentration of a gas under measurement in a manner similar to that used for the gas sensor described in (6), the gas sensor of embodiment (12) provides effects similar to those provided by the gas sensor described in (6).

Further, since the gas sensor of embodiment (12) measures the flow rate of the gas under measurement in accordance with the gas-flow-rate measurement method described in (9), the gas sensor of embodiment (12) provides effects similar to those described in relation to (9).

Moreover, since embodiment (12) enables measurement of pressure and flow rate of a gas under measurement by use of a single gas sensor, cost and installation space of the gas sensor can be decreased.

In particular, the gas sensor of embodiment (12) calculates gas flow rate on the basis of a measured gas pressure, through use of, for example, a map. Therefore, hardware portions for measurement of gas flow can be reduced. Accordingly, the gas sensor of embodiment (12) can be made compact.

(13) A gas sensor which comprises means for detecting the concentration of a specific gas contained in a gas under measurement by use of the ultrasonic-wave propagation time measurement method described in any one of (1) to (5), means for detecting the pressure of the gas under measurement by use of the gas-pressure measurement method described in (7) or (8), and means for detecting the flow rate of the gas under measurement by use of the gas-flow-rate measurement method described in (9).

Since the gas sensor of embodiment (13) measures the concentration of a gas under measurement in a manner similar to that used for the gas sensor described in (6), the gas sensor of embodiment (13) provides effects similar to those provided by the gas sensor described in (6).

Since the gas sensor of embodiment (13) measures the pressure of the gas under measurement in a manner similar to that used for the gas sensor described in (10), the gas sensor of embodiment (13) provides effects similar to those provided by the gas sensor described in (10).

Moreover, since the gas sensor of embodiment (13) measures the flow rate of a gas under measurement in accordance with the gas-flow-rate measurement method described in (9), the gas sensor of embodiment (13) provides effects similar to those described in relation to (9).

Since embodiment (13) enables measurement of concentration of a specific component of a gas under measurement and pressure and flow rate of the gas under measurement by use of a single gas sensor, cost and installation space of the gas sensor can be decreased.

(14) The gas sensor described in (10), wherein the gas under measurement is a gas within an intake pipe or canister purge line in an internal combustion engine.

Since the gas sensor of embodiment (14) can measure gas pressure within the intake pipe or canister purge line, the gas sensor can be used for optimal control of the ratio between fuel and air supplied to the internal combustion engine.

The following example method may be employed for such control. The gas pressure within the intake pipe or canister purge line is measured by using the gas sensor of embodiment (13); the flow rate of the gas flowing within the intake pipe or canister purge line is calculated from the measured pressure (by the method described in (9)); and at the same time, the concentration of vaporized fuel in the gas is measured by use of another method. From the gas flow-rate and the concentration of vaporized fuel, the quantity of vaporized fuel supplied from the intake pipe to the internal combustion engine (hereinafter referred to as "vaporized-fuel quantity") can be calculated.

Accordingly, the total quantity of fuel supplied to the internal combustion engine can be accurately calculated from the vaporized-fuel quantity and a known quantity of fuel supplied from an injector; and on the basis of the total quantity, the fuel/air ratio within a gas which takes part in combustion within the internal combustion engine can be controlled properly. As a result, toxic components contained in exhaust gas can be decreased in concentration.

(15) The gas sensor described in (11), wherein the gas under measurement is a gas within an intake pipe or canister purge line in an internal combustion engine; and a component of the gas under measurement is fuel for the internal combustion engine.

When a flow rate of a gas flowing within the intake pipe or canister purge line and the concentration of vaporized fuel within the gas are measured by using the gas sensor of embodiment (15), the quantity of vaporized fuel supplied from the intake pipe to the internal combustion engine can be calculated from the gas flow rate and the concentration of vaporized fuel.

Accordingly, as in embodiment (14), the fuel/air ratio within a gas which takes part in combustion within the internal combustion engine can be controlled properly, whereby toxic components contained in exhaust gas can be decreased in concentration.

(16) The gas sensor described in (12), wherein the gas under measurement is a gas within an intake pipe or canister purge line in an internal combustion engine.

When the flow rate of the gas flowing within the intake pipe or canister purge line is measured by using the gas sensor of embodiment (16), and the concentration of vaporized fuel in the gas is measured by use of another method, the quantity of vaporized fuel supplied from the intake pipe to the internal combustion engine can be calculated from the gas flow-rate and the concentration of vaporized fuel.

Accordingly, as in embodiment (14), the air/fuel ratio within a gas which takes part in combustion within the internal combustion engine can be controlled properly, whereby toxic components contained in exhaust gas can be decreased in concentration.

(17) The gas sensor described in (13), wherein the gas under measurement is a gas within an intake pipe or canister purge line in an internal combustion engine; and a component of the gas under measurement is fuel for the internal combustion engine.

When the flow rate of a gas flowing within the intake pipe or canister purge line and the concentration of vaporized fuel within the gas are measured by using the gas sensor of embodiment (17), the quantity of vaporized fuel supplied from the intake pipe to the internal combustion engine can be calculated from the gas flow rate and the concentration of vaporized fuel.

Accordingly, as in embodiment (14), the air/fuel ratio within a gas which takes part in combustion within the internal combustion engine can be controlled properly, whereby toxic components contained in exhaust gas can be decreased in concentration.

BRIEF DESCRIPTION OF THE DRAWINGS

FIG. 2(a) shows a state where the concentration of vaporized fuel is low and FIG. 2(b) shows a state where the concentration of vaporized fuel is high.

Figure 1:
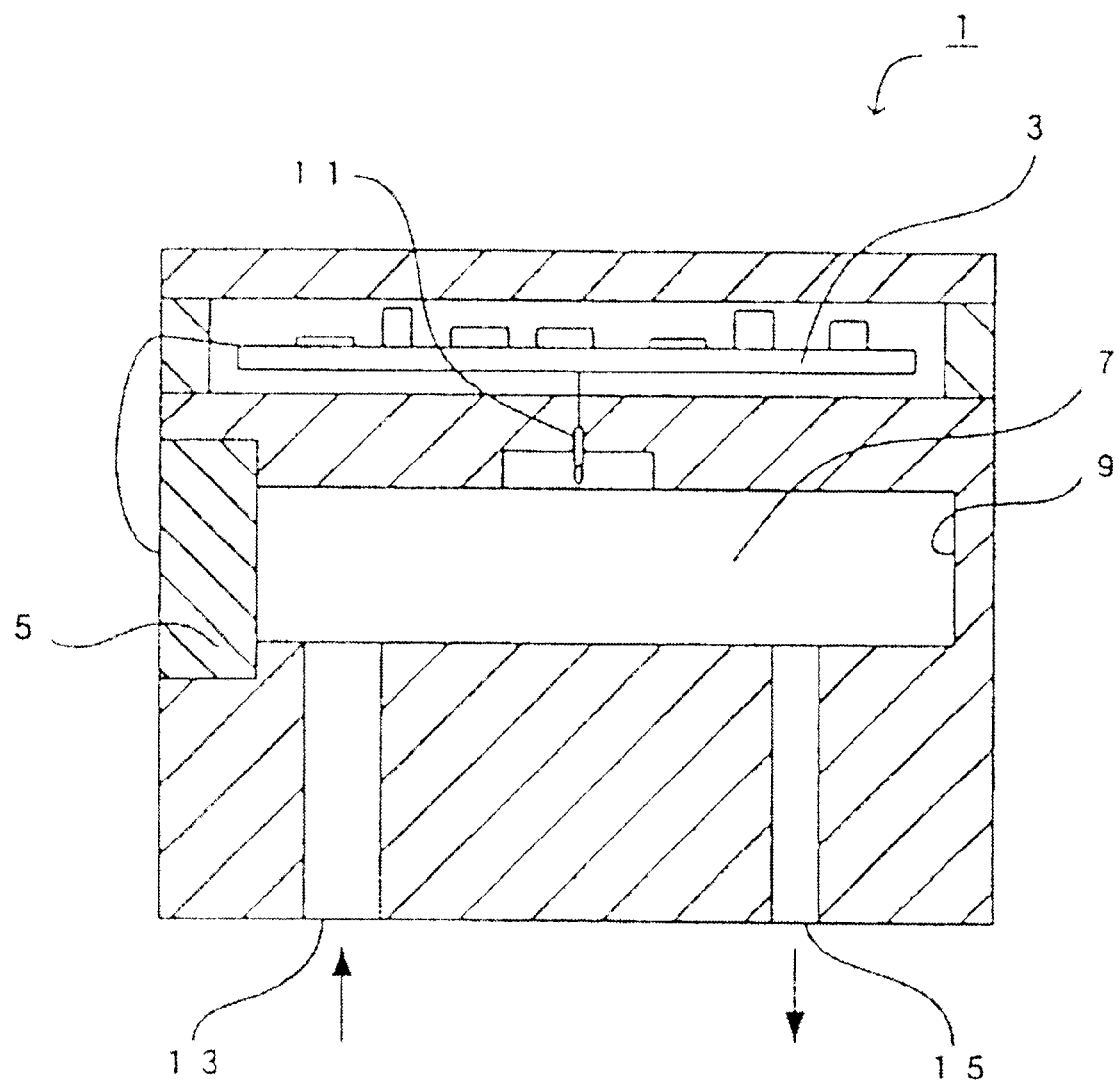
FIG. 1 is an explanatory view showing a gas concentration sensor of the first embodiment.

Reference numerals are used to identify items shown in the drawings as follows:

1 gas concentration sensor
3 drive/calculation circuit
5 ultrasonic-wave transmission/reception element (ultrasonic element)
7 measurement chamber
9 reflection surface
11 thermistor
101 gas concentration/pressure sensor
110 intake pipe
111 engine
112 gasoline tank
114 canister
115 canister purge line

DESCRIPTION OF THE PREFERRED EMBODIMENTS

First Embodiment

The present embodiment is directed to detection of the concentration of a specific gas (vaporized fuel) in air, which is a gas under measurement (i.e., atmosphere to be measured), by use of a gas sensor (gas concentration sensor) utilizing the ultrasonic-wave propagation-time measuring method.

a) First, the structure of the gas concentration sensor according to the present embodiment will be described.

The gas concentration sensor of the present embodiment is an ultrasonic-type gas concentration sensor in which ultrasonic waves are generated by use of a piezoelectric element; in particular, a common ultrasonic-wave transmission/reception element (hereinafter also referred to as an "ultrasonic element") is used for transmission and reception of ultrasonic waves.

Specifically, as shown in FIG. 1, the gas concentration sensor 1 comprises a drive/calculation circuit 3 for performing drive and calculation required for detection of gas concentration; an ultrasonic element 5 for effecting transmission and reception of ultrasonic waves; a measurement chamber 7 into which intake gas is introduced, which is a gas under measurement and containing a specific gas; a reflection surface 9 which is separated by a predetermined distance from the ultrasonic element 5 such that the reflection surface 9 faces the ultrasonic element 5 to thereby reflect ultrasonic waves within the measurement chamber 7; a thermistor 11 for measuring the temperature within the measurement chamber 7; a gas inlet port 13 into which intake gas flows; and a gas outlet port 15 through which the intake gas exits.

b) The principle of operation of the gas concentration sensor 1 will next be described.

Figure 2:
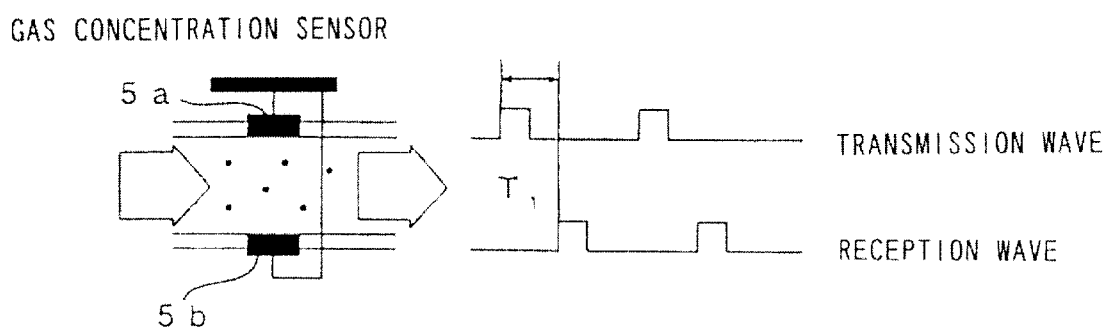
FIGS. 2(a) and 2(b) are explanatory views showing the basic principle of the gas concentration sensor of the first embodiment, where
Figure 2:
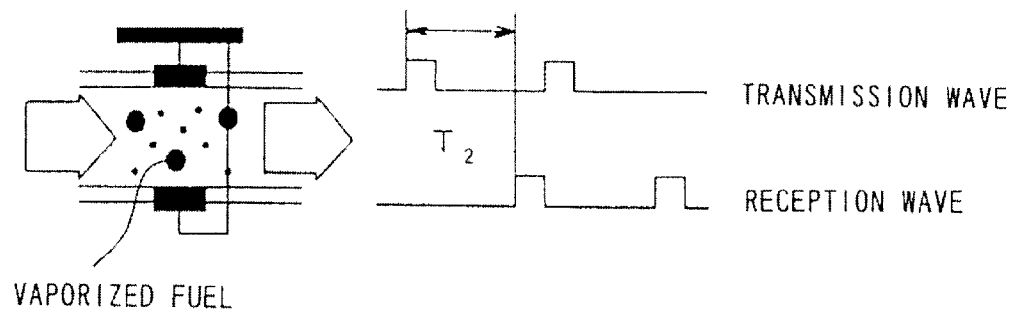

In FIG. 2, in order to facilitate understanding, the ultrasonic element 5 is illustrated as having separate transmission and reception elements 5a and 5b. However, in the present invention, the ultrasonic element 5 can have a common transmission/reception element.

(1) As shown in FIG. 2, when concentration measurement is performed by use of the gas concentration sensor 1, an ultrasonic wave is transmitted from the transmission device 5a, and the ultrasonic wave is received by the reception device 5b. At this time, a shift is produced between the transmission wave and the reception wave in accordance with a propagation time which varies with concentration of a specific gas (e.g., vaporized fuel) within the intake gas.

When the concentration of vaporized fuel is low, as in FIG. 2(a), a relatively short propagation time $T_1$ results; i.e., a relatively small shift is produced between the transmission wave and the reception wave. In contrast, when the concentration of vaporized fuel is high, as shown in FIG. 2(b), a relatively long propagation time $T_2$ results; i.e., a relatively large shift is produced between the transmission wave and the reception wave. Accordingly, the gas concentration can be detected by detecting a sensor output which corresponds to the propagation time.

(2) Next, general operation of the gas concentration sensor 1 which operates on the basis of the above-described principle will be described.

A gas under measurement flows from the gas inlet port 13 into the measurement chamber 7 and then flows to the outside through the gas outlet port 15. During such flow, the concentration of a specific gas contained in the gas under measurement is measured within the measurement chamber 7. Specifically, when the propagation time of an ultrasonic wave within the measurement chamber 7 is measured, an ultrasonic wave is first transmitted from the ultrasonic element 5. The transmitted ultrasonic wave passes through the gas under measurement and is reflected by the reflection surface 9. The reflected wave passes through the gas under measurement and is received by the same ultrasonic element 5.

As will be described in detail below, the drive/calculation circuit 3 calculates the propagation time between the timing of transmission (emission time) of a transmission wave and the timing of reception (arrival time) of a corresponding reception wave. The drive/calculation circuit 3 also detects the temperature within the measurement chamber 7 on the basis of a signal from the thermistor 11.

Since the propagation time depends on gas concentration and is affected by temperature, the drive/calculation circuit 3 obtains the concentration of a specific gas from a predetermined map and in accordance with a procedure which will be described below.

c) Next, the procedure for detection of gas concentration will be described in more detail, together with processing performed in the drive/calculation circuit 3. It is to be noted that in FIG. 3 the internal structure of a microprocessor 21 is illustrated functionally.

Figure 3:
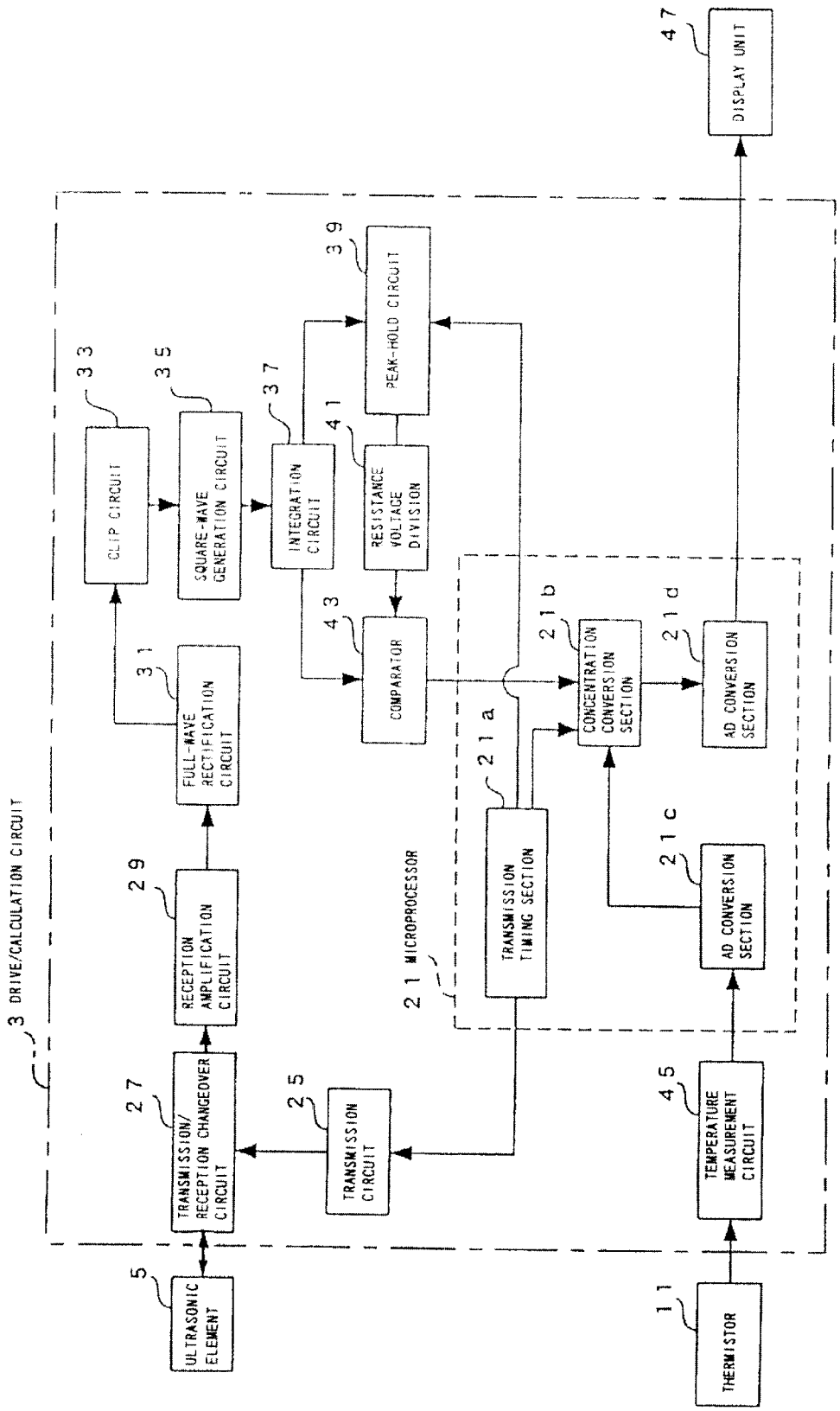
FIG. 3 is a block diagram showing the electrical configuration of the gas concentration sensor of the first embodiment.

(i) As shown in the block diagram of FIG. 3, a transmission timing section 21a of the microprocessor 21 produces a signal indicating a transmission timing, which is sent to a transmission circuit 25. An electrical pulse signal output from the transmission circuit 25 is transmitted to the ultrasonic element 5 via a transmission/reception changeover circuit 27. The ultrasonic element 5 converts the electrical pulse signal to an ultrasonic wave (transmission wave) and transmits it toward the reflection surface 9.

A pulse energy (reception wave) received by the ultrasonic element 5 after being reflected by the reflection surface 9 is converted to an electrical signal by the ultrasonic element 5.

At this point of time, the transmission/reception changeover circuit 27 switches the signal path from the transmission circuit 25 to a reception amplification circuit 29. Therefore, the electrical signal (indicating the reception wave) from the ultrasonic element 5 is fed to a full-wave rectification circuit 31 so as to undergo full-wave rectification. A clip circuit 33 removes noise from the resultant signal in order to obtain a noise-free waveform, on the basis of which a square-wave generation circuit 35 generates a square wave. It is to be noted that full-wave rectification decreases the degree of unevenness of the produced square wave.

An integration circuit 37 integrates the square wave to thereby obtain an integral value, and a peak-hold circuit 39 holds a peak value of the integral value. Subsequently, a resistance-voltage-division circuit 41 obtains half the peak value and outputs the same as a threshold level (reference value) for a comparator 43.

Figure 4:
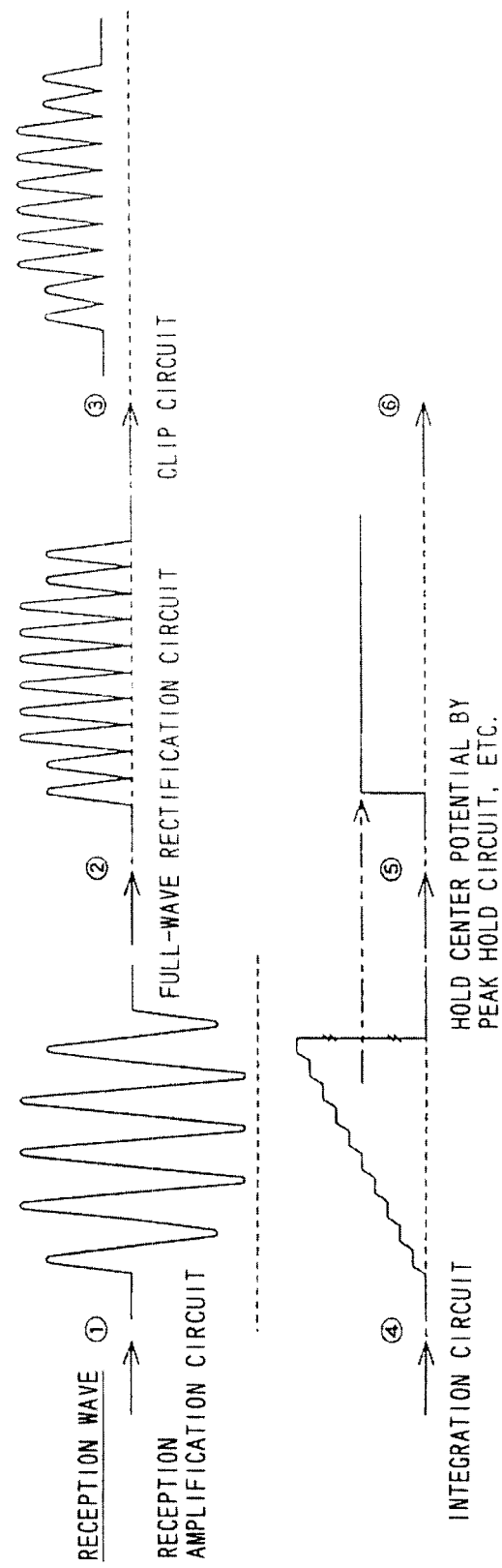
FIG. 4 is an explanatory view relating to the first embodiment and showing processing of a reception wave.

(ii) FIG. 4 shows variations in the reception wave up to this point. The reception wave is amplified by the reception amplification circuit 29 (see (1) in FIG. 4), subjected to full-wave rectification performed by the full-wave rectification circuit 31 (see (2) in FIG. 4), subjected to noise cut performed by the clip circuit 33 (see (3) in FIG. 4), and integrated by the integration circuit 37 (see (4) in FIG. 4). On the basis of a resultant integral value, the peak-hold circuit 39 and the resistance-voltage-division circuit 41 hold a center potential which serves as a threshold level (see (5) in FIG. 4).

(iii) Referring back to FIG. 3, when an actual gas concentration is detected, integration of a reception wave is effected in steps similar to those for setting the above-described threshold level. Subsequently, the comparator 43 judges whether the integral value has attained the threshold level. When the integral value is judged to have attained the threshold level, the comparator 43 transmits to a concentration conversion section 21b of the microprocessor 21 a signal which reports the judgement result.

The time of reception of the signal is a reception timing (arrival time). It is to be noted that the transmission timing (emission time) is transmitted in advance from the transmission timing section 21a to the concentration conversion section 21b and stored therein.

Upon reception of the signal from the comparator 43, the concentration conversion section 21b of the microprocessor 21 calculates a period of time (i.e., propagation time) from the emission time to a time when the integral value attains the threshold level.

(iv) Meanwhile, the signal from the thermistor 11 is input to an AD conversion section 21c via a temperature measurement circuit 45, and a signal representing the temperature is input to the concentration conversion section 21b.

(v) Accordingly, the concentration conversion section 21b obtains the concentration of the specific gas from the propagation time, while taking into consideration the temperature conditions.

More specifically, a sonic velocity C is first calculated from the propagation time by use of the following equation (1):

Sonic velocity C=(round-trip distance between the element surface and the reflection surface)/propagation time    (1)

Figure 5:
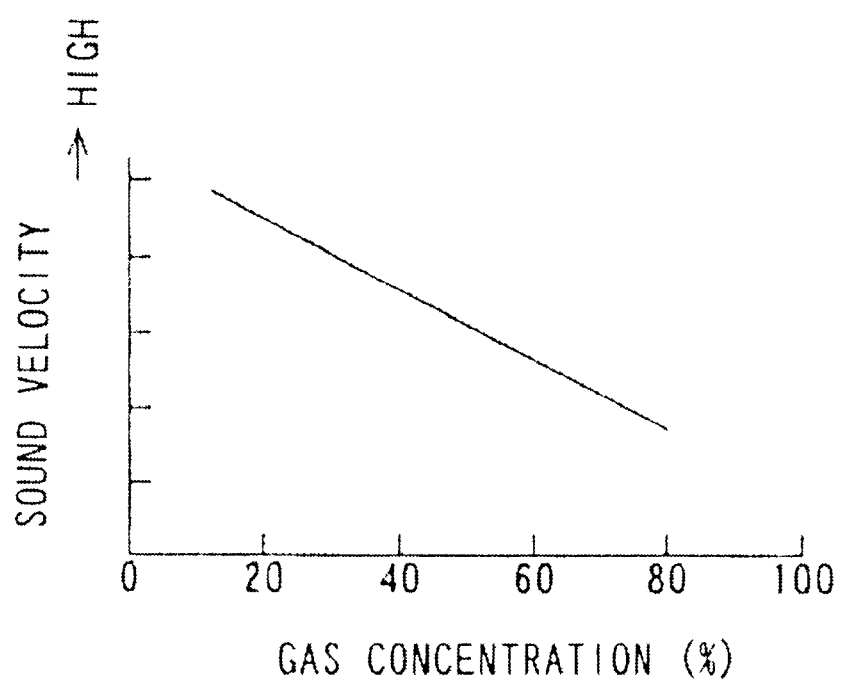
FIG. 5 is a graph relating to the first embodiment and showing a map for obtaining gas concentration.

Next, since the sonic velocity C varies with temperature, through use of the measured temperature, the sonic velocity C is converted to a sonic velocity KC measured at a reference temperature. Subsequently, gas concentration is obtained by use of a map (e.g., a map as shown in FIG. 5) which shows the relationship (proportional relationship) between sonic velocity KC and gas concentration.

The thus-obtained gas concentration is converted to an analog value by an AD conversion section 21d and is displayed on, for example, a display unit 47.

As described above, in the present embodiment, half the maximum integral value is set as a threshold level; during measurement of propagation time, a period of time between the timing of transmission of a transmission wave and a time when the integral value of a reception wave attains the threshold level is measured as a propagation time; and gas concentration is detected on the basis of the propagation time and in consideration of temperature. Therefore, the detection is hardly affected by a decrease in pressure of atmospheric air (gas under measurement), and thus the gas concentration can be detected accurately at all times.

That is, in the conventional technique (fixed threshold level), when the pressure of a gas under measurement decreases, a reception wave attenuates, and an integral value decreases accordingly, resulting in an increase in propagation time, which renders measurement of gas concentration inaccurate. By contrast, in the measurement method according to the present embodiment, even when the reception wave attenuates, measurement of propagation time; i.e., measurement of gas concentration, can be performed accurately, because half the integrated value is always used as a threshold level (used for judgement of arrival time).

In the present embodiment, within a range in which an integral value varies from the start of integration and attains the maximum, half the maximum value is used as the threshold level. However, an arbitrary point within the range can be used as the threshold level.

Further, the arbitrary point may be determined by use of the microprocessor. For example, an integral value is converted to a digital signal which is then input to the microprocessor in order to set an appropriate point as the threshold level. In this case, for detection of gas concentration, an integral value is converted to a digital signal, which is then compared with the threshold level in order to measure propagation time.

d) Next will be described an evaluation test performed in order to confirm the effects of the gas concentration sensor 1 of the present embodiment.

Figure 6:
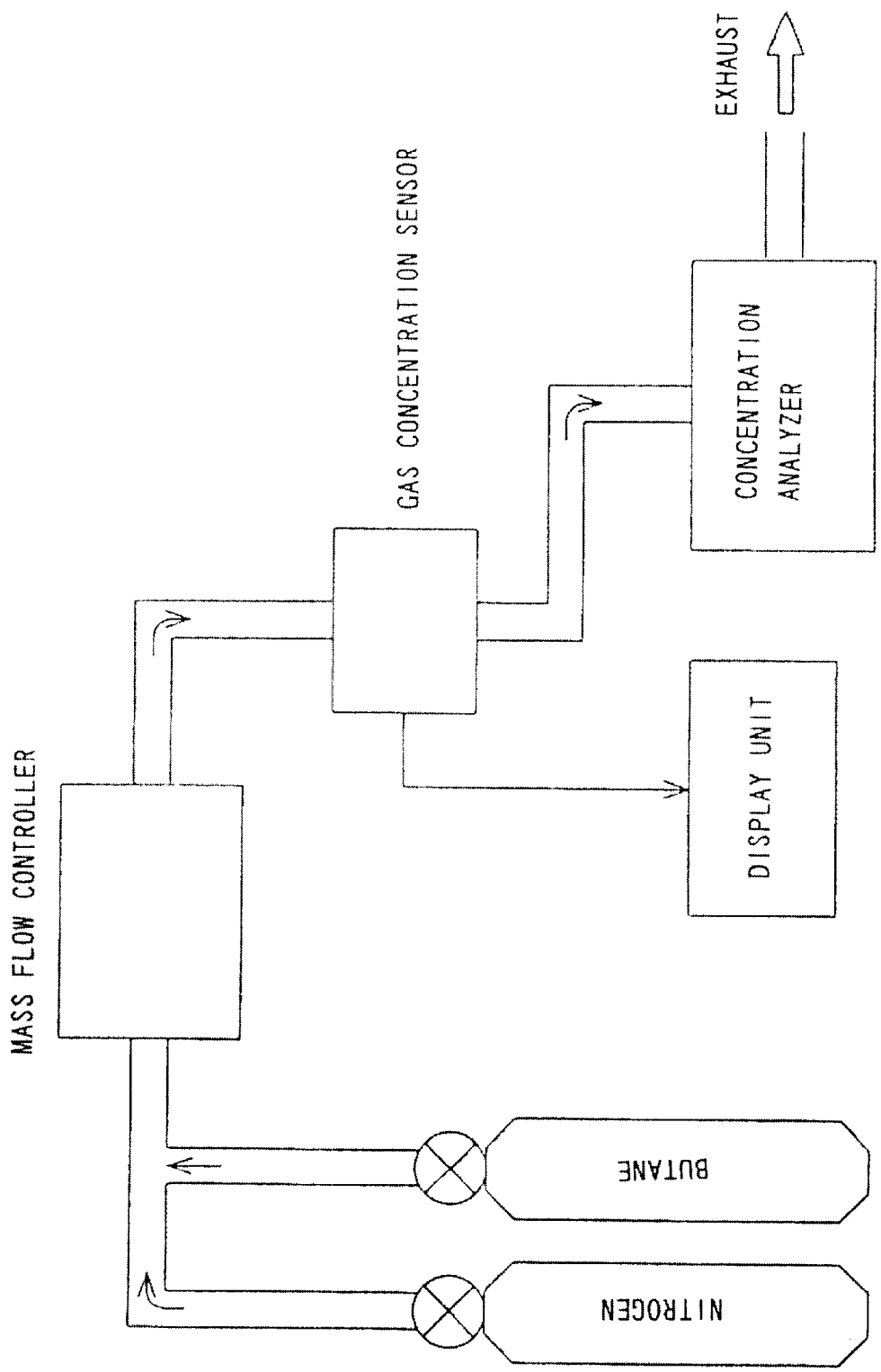
FIG. 6 is an explanatory view relating to the first embodiment and showing an evaluation apparatus for the gas concentration sensor.

(1) An evaluation apparatus as shown in FIG. 6 was used for the evaluation test. The evaluation apparatus comprises a mass flow controller for adjusting gas flow rate; a gas concentration sensor to be evaluated; a display unit for displaying gas concentration; and a concentration analyzer (e.g., an infrared concentration analyzer) for confirming concentration.

Gas mixtures (gas under measurement) of butane (specific gas) and nitrogen (base gas) of different butane concentrations were prepared, and each was supplied to the gas concentration sensor in a respective test run performed at 25° C. The thus-measured concentration was displayed on the display unit, and correct concentration was measured by use of the concentration analyzer. The results are shown in Table 1 below.

TABLE 1

| | Detection results (vol. %) | |
| --- | --- | --- |
| No. | Gas concentration sensor | Concentration analyzer |
| 1 | 20.1 | 20.4 |
| 2 | 39.8 | 40.3 |
| 3 | 80.8 | 80.1 |

As is apparent from Table 1, the detection values of the gas concentration sensor of the present embodiment are substantially the same as those obtained through use of the concentration analyzer, and therefore the gas concentration sensor of the present embodiment is found to be considerably accurate.

(2) Separately, an evaluation test was performed while the pressure (atmospheric pressure) of the gas mixture was varied.

This evaluation test was performed by use of the gas concentration sensor of the present embodiment (the threshold level was half an integration value) and a conventional gas concentration sensor (the threshold level was fixed). While the pressure of the gas mixture was varied, propagation time at the time of gas-concentration detection was measured at 25° C., and a propagation time variation ratio was calculated. The term "propagation time variation ratio" refers to percent variation in propagation time from a theoretical value.

Figure 7:
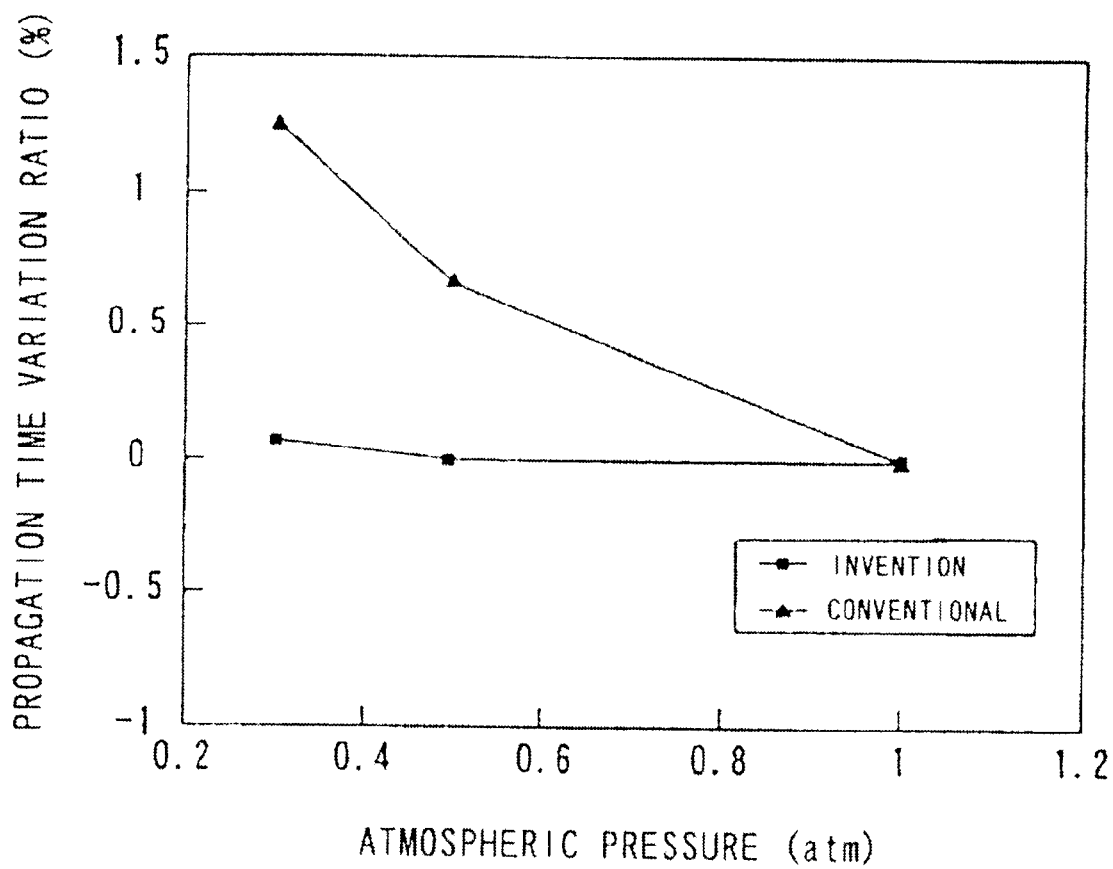
FIG. 7 is a graph relating to the first embodiment and showing a ratio of variation in propagation time when the atmospheric pressure is changed.

The results are shown in FIG. 7. In the conventional gas concentration sensor, errors involved in propagation time increase as atmospheric pressure decreases. By contrast, in the gas concentration sensor of the present invention, errors are hardly produced even when atmospheric pressure changes.

Similar results are obtained even when the ultrasonic element is composed of separate transmission and reception elements.

Second Embodiment

Next, a gas sensor (gas concentration sensor) of a second embodiment will be described. Descriptions are simplified for portions similar to those of the first embodiment.

Figure 8:
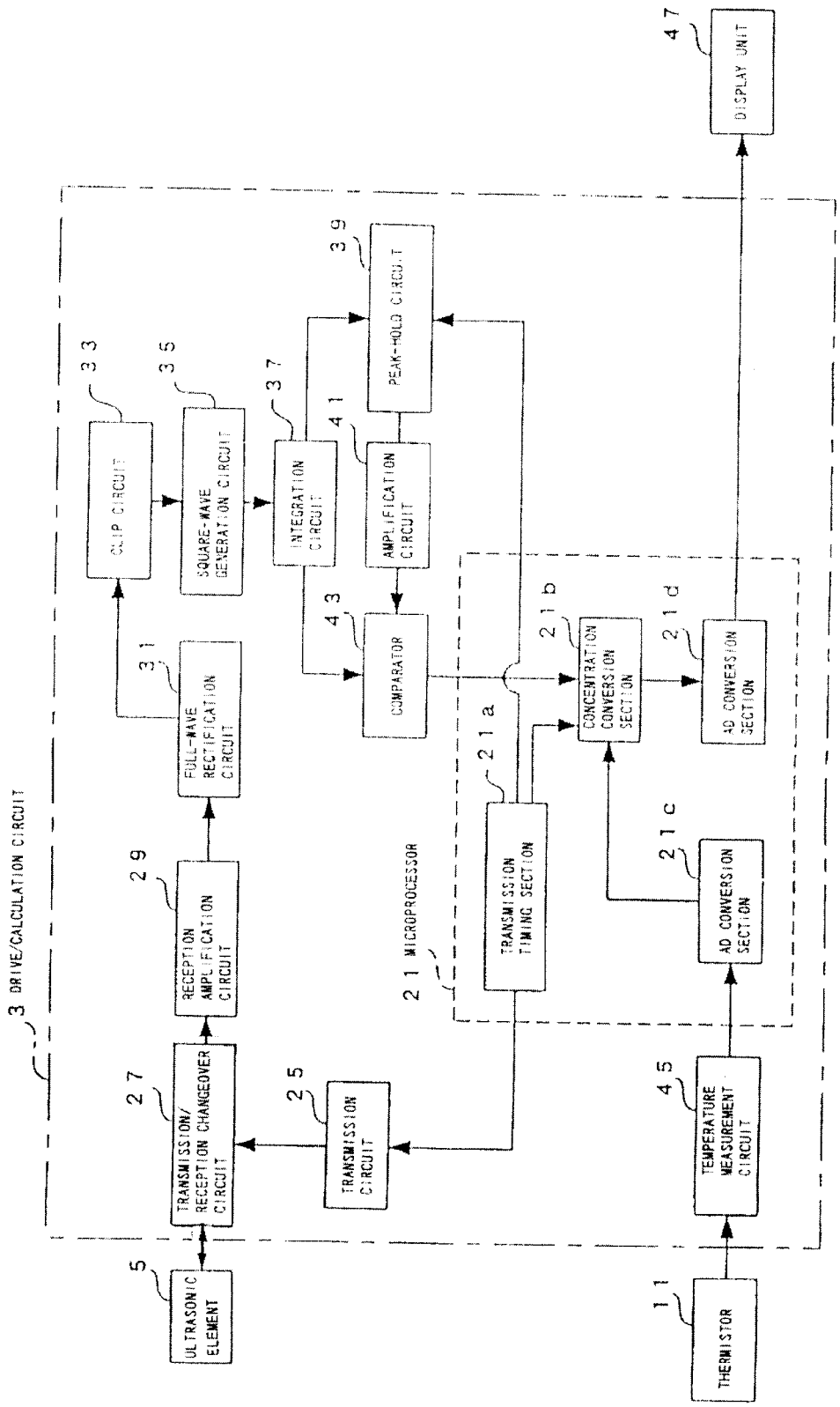
FIG. 8 is a block diagram showing the electrical configuration of a gas concentration sensor of the second embodiment.

Although the gas concentration sensor of the second embodiment has a structure similar to that of the first embodiment, as shown in FIG. 8, the sensor of the second embodiment differs greatly from that of the first embodiment in that an amplification circuit 51 is used in place of the resistance-voltage-division circuit.

a) The procedure for detection of gas concentration in the present embodiment will be described with reference to the block diagram of FIG. 8.

(i) First, the transmission timing section 21 a of the microprocessor 21 produces a signal indicating a transmission timing, which is sent to the transmission circuit 25. An electrical pulse signal output from the transmission circuit 25 is transmitted to the ultrasonic element 5 via the transmission/reception changeover circuit 27. The ultrasonic element 5 converts the electrical pulse signal to an ultrasonic wave (transmission wave) and transmits it toward the reflection surface 9.

A pulse energy (reception wave) received by the ultrasonic element 5 after being reflected by the reflection surface 9 is converted to an electrical signal by the ultrasonic element 5.

At this point in time, the transmission/reception changeover circuit 27 switches the signal path from the transmission circuit 25 to the reception amplification circuit 29. Therefore, the electrical signal (indicating the reception wave) from the ultrasonic element 5 is fed to the full-wave rectification circuit 31 so as to undergo full-wave rectification. The clip circuit 33 removes noise from a resultant signal in order to obtain a noise-free waveform, on the basis of which the square-wave generation circuit 35 generates a square wave.

The integration circuit 37 integrates the square wave to thereby obtain an integral value, and the peak-hold circuit 39 holds a peak value of the integral value. Subsequently, the amplification circuit 51 adjusts its output voltage in accordance with the peak value and outputs the output voltage as a threshold level (reference value) for the comparator 43. For example, the threshold level is set to half the peak voltage.

(ii) When an actual gas concentration is detected, integration of a reception wave is effected in steps similar to those for setting the above-described threshold level. Subsequently, the comparator 43 judges whether the integral value has attained the threshold level. When the integral value is judged to have attained the threshold level, the comparator 43 transmits to the microprocessor 21 a signal which reports the judgement result.

Upon reception of the signal from the comparator 43, the concentration conversion section 21b of the microprocessor 21 calculates a period of time (i.e., propagation time) from the emission time to a time when the integral value attains the threshold level.

(iii) Meanwhile, the signal from the thermistor 11 is input to the AD conversion section 21c via the temperature measurement circuit 45, and a signal representing temperature is input to the concentration conversion section 21b.

(v) Accordingly, the concentration conversion section 21b obtains the concentration of the specific gas from the propagation time, while taking into consideration the temperature conditions.

More specifically, a sonic velocity C is first calculated from the propagation time by use of the above-described equation (1), and through use of the measured temperature, the sonic velocity C is converted to a sonic velocity KC measured at a reference temperature. Subsequently, gas concentration is obtained by use of a map which shows the relationship between sonic velocity KC and gas concentration.

As described above, in the present embodiment, the threshold voltage is adjusted by the amplification circuit 51 in accordance with the peak voltage, and propagation time is measured from an integral value of a reception wave by use of the threshold voltage Therefore, as in the first embodiment, gas concentration can be detected accurately without influence of pressure variation. In addition, in the present embodiment, since the threshold voltage can be changed easily, conditions for easiest measurement can be easily set in accordance with measurement conditions.

d) Next will be described an evaluation test performed in order to confirm the effects of the gas concentration sensor 1 of the present embodiment.

In the evaluation test, evaluation was performed by use of an evaluation apparatus similar to that used in the first embodiment, while the pressure (atmospheric pressure) of the gas mixture was varied.

Specifically, this evaluation test was performed using the gas concentration sensor of the present embodiment (the threshold level was half the peak voltage) and a conventional gas concentration sensor (the threshold level was fixed). While the pressure of the gas mixture was varied, propagation time at the time of gas-concentration detection was measured at 25° C., and a propagation time variation ratio was calculated.

Figure 9:
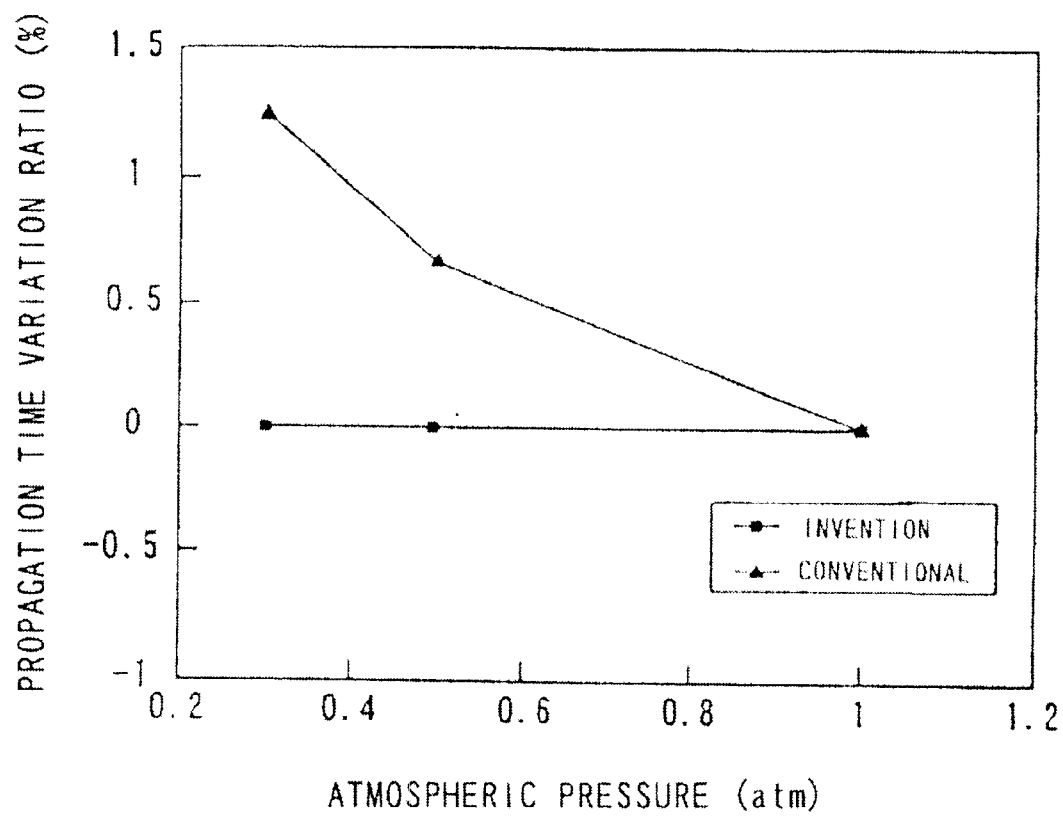
FIG. 9 is a graph relating to the second embodiment and showing a ratio of variation in propagation time when the atmospheric pressure is changed.

The results are shown in FIG. 9. In the conventional gas concentration sensor, errors involved in propagation time increase as atmospheric pressure decreases. By contrast, in the gas concentration sensor of the present invention, errors are hardly produced even when atmospheric pressure changes.

Third Embodiment

Next, a gas sensor (gas concentration sensor) of a third embodiment will be described. Descriptions are simplified for portions similar to those of the second embodiment.

Figure 10:
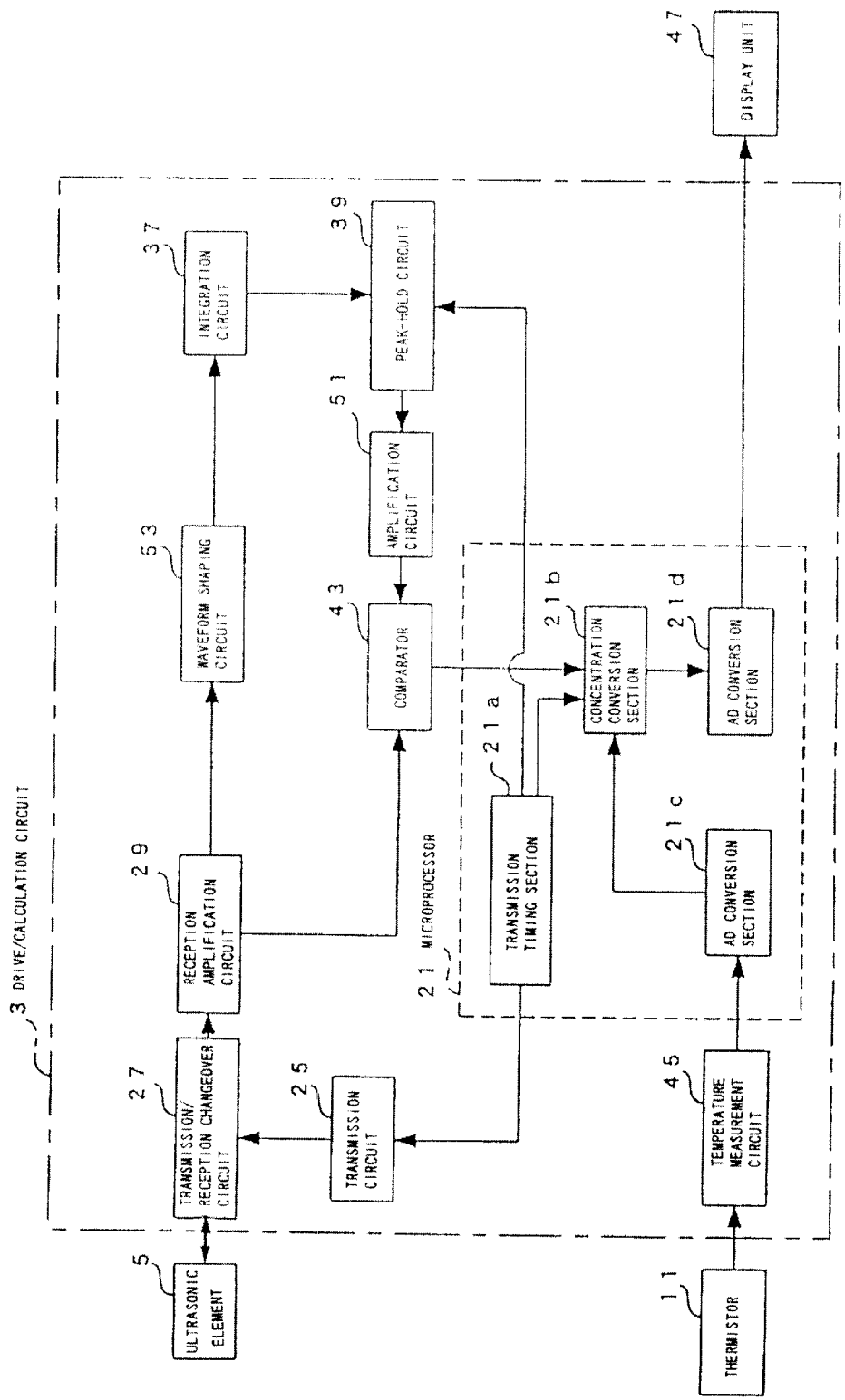
FIG. 10 is a block diagram showing the electrical configuration of a gas concentration sensor of the third embodiment.

Although the gas concentration sensor of the third embodiment has a structure similar to that of the gas concentration sensor of the second embodiment, as shown in FIG. 10, the sensor of third embodiment differs in structure from that the second embodiment in, for example, a waveform-shaping circuit. In addition, the third embodiment is characterized in that actual measurement employs not an integral value of a reception wave, but the reception wave itself.

The procedure for detection of gas concentration in the present embodiment will be described with reference to the block diagram of FIG. 10.

(i) First, the transmission timing section 21 a of the microprocessor 21 produces a signal indicating transmission timing, which is sent to the transmission circuit 25. An electrical pulse signal output from the transmission circuit 25 is transmitted to the ultrasonic element 5 via the transmission/reception changeover circuit 27. The ultrasonic element 5 converts the electrical pulse signal to an ultrasonic wave (transmission wave) and transmits it toward the reflection surface 9.

A pulse energy (reception wave) received by the ultrasonic element 5 after being reflected by the reflection surface 9 is converted to an electrical signal by the ultrasonic element 5.

At this point in time, the transmission/reception changeover circuit 27 switches the signal path from the transmission circuit 25 to the reception amplification circuit 29. Therefore, the electrical signal (indicating the reception wave) from the ultrasonic element 5 is fed to a waveform-shaping circuit 53, in which a portion of the waveform of the signal is cut. The integration circuit 37 integrates the thus-obtained signal to thereby obtain an integral value, and the peak-hold circuit 39 holds a peak value of the integral value.

Subsequently, the amplification circuit 51 adjusts its output voltage in accordance with the peak value and outputs the output voltage as a threshold level (reference value) for the comparator 43. For example, the threshold level is set to half the peak voltage.

(ii) When actual gas concentration is detected, a reception wave is amplified by the reception amplification circuit 29. The comparator 43 judges whether the amplified reception wave has attained the threshold level. When the amplified reception wave is judged to have attained the threshold level, the comparator 43 transmits to the microprocessor 21 a signal which reports the judgement result.

Upon reception of the signal from the comparator 43, the concentration conversion section 21b of the microprocessor 21 calculates a period of time (i.e., propagation time) from the emission time to the time when the amplified reception wave attains the threshold level. (iii) Meanwhile, the signal from the thermistor 11 is input to the AD conversion section 21c via the temperature measurement circuit 45, and a signal representing the temperature is input to the concentration conversion section 21b.

(iv) Accordingly, the concentration conversion section 21b obtains the concentration of the specific gas from the propagation time, while taking into consideration the temperature conditions.

More specifically, a sonic velocity C is first calculated from the propagation time by use of the above described equation (1), and through use of the measured temperature, the sonic velocity C is converted to a sonic velocity KC measured at a reference temperature. Subsequently, gas concentration is obtained by use of a map which shows the relationship between sonic velocity KC and gas concentration.

As described above, in the present embodiment, the threshold voltage is adjusted by the amplification circuit 51 in accordance with peak voltage, and propagation time is measured through use of an amplified reception wave.

Therefore, effects similar to those achieved in the second embodiment are achieved. In addition, since integration of a reception wave is not required for gas-concentration detection, the amount of calculation processing decreases.

Fourth Embodiment

A fourth embodiment of the present invention relates to a fuel supply system of an automobile engine, the fuel supply system being equipped with a gas sensor (gas concentration/pressure sensor) which measures the concentration of vaporized fuel through utilization of propagation time of an ultrasonic wave and measures the pressure of an atmospheric gas (gas under measurement) through utilization of strength of an ultrasonic reception wave.

a) First, the structure of the automobile-engine fuel supply system of the fourth embodiment will be described with reference to FIG. 11.

The automobile-engine fuel supply system of the fourth embodiment mainly comprises an engine 111; an ECU 109 for controlling operation conditions of the engine 111; a gasoline tank 112 for storing fuel to be supplied to the engine 111; an injector 113 for adjusting the amount of fuel supplied to the engine 111; an intake pipe 110 for supplying air to the engine 111; an air-flow sensor 119 for detecting and adjusting the flow rate of air flowing through the intake pipe 110; a canister 114 for temporarily trapping fuel vaporized in the gasoline tank 112; a purge line 115 for feeding vaporized fuel accumulated in the canister 114 to the intake pipe 110; a purge valve 118 for opening and closing the purge line 115; an exhaust pipe 116 for exhausting exhaust gas discharged from the engine 111; an $O_2$ sensor 117 for measuring $O_2$ concentration in the exhaust pipe 116; and a gas concentration/flow rate sensor 101 for detecting vaporized fuel concentration and atmospheric gas pressure within the pipe (a sensor 101a disposed at the purge line 115 and a sensor 101b disposed at the intake pipe).

In the fuel supply system of the fourth embodiment, vaporized fuel generated in the gasoline tank 112 is temporarily trapped in the canister 114, and is sucked from the canister 114 by means of negative pressure in the intake pipe 110. A gas mixture (purge gas) of the vaporized fuel and air reaches the intake pipe 110 via the purge line 115 and is then fed into the engine 111.

On the basis of signals fed from the gas concentration/pressure sensor 101, the $O_2$ sensor 117, and the engine 111, the ECU 109 adjusts the openings of the injector 113, the air-flow sensor 119, and the purge valve 118 to thereby control the operation conditions of the engine 111.

In particular, on the basis of the gas flow rate and vaporized fuel concentration within the intake pipe 110 and the purge line 115 detected by the gas concentration/pressure sensor 101, the ECU 109 calculates an amount of vaporized fuel introduced from the intake pipe 110 into the engine 111 and, on the basis of the amount of vaporized fuel, controls the injector 113 and the air-flow sensor 119 in order to optimize the ratio between fuel and air introduced into the engine 111 (fuel/air ratio).

b) The gas concentration/pressure sensor 101 of the fourth embodiment has a structure similar to that of the gas concentration sensor of the first embodiment. However, as will be described later, the concentration/pressure sensor 101 differs from the gas concentration sensor of the first embodiment in the structure of the drive/calculation circuit 3 shown in FIG. 1.

c) Next, the principle of operation of the gas concentration/pressure sensor 101 will be described.

(1) The principle of measurement of concentration of vaporized fuel within an atmospheric gas is the same as that of the gas concentration sensor 1 of the first embodiment.

(2) Next, the principle of measurement of pressure of the atmospheric gas will be described.

An ultrasonic wave is transmitted from the transmission element 5b and is received by the reception element 5a.

Figure 13:
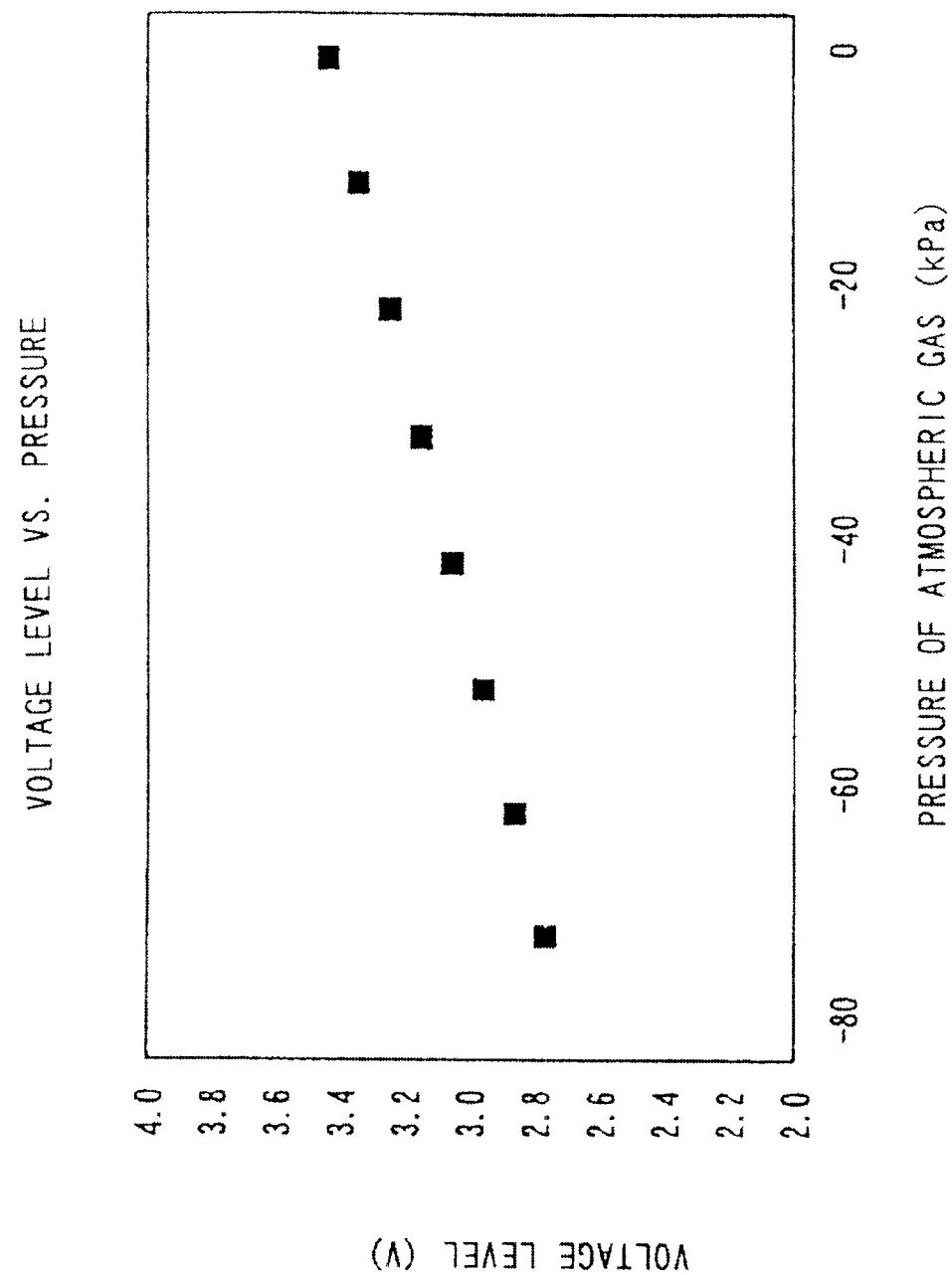
FIG. 13 is a graph relating to the fourth embodiment and showing a map for obtaining gas pressure.

At this time, the strength of the reception wave is lower than that of the transmission wave, due to attenuation, which increases as the pressure of the atmospheric gas decreases. Accordingly, when the strength of the transmission wave is maintained constant, as shown in FIG. 13, the strength of the reception wave decreases with the pressure of the atmospheric gas.

Taking advantage of this phenomenon, the pressure of the atmospheric gas can be detected on the basis of an output of the sensor corresponding to the strength of the reception wave.

An integral value obtained through integration of a reception wave or a portion thereof, or a maximum amplitude of the reception wave or a portion thereof, can be used as a parameter which indicates the strength of the reception wave or a portion thereof. In FIG. 13, the integral value is used.

Further, the gas concentration/pressure sensor 101 can calculate the flow rate of the atmospheric gas through use of the pressure of the atmospheric gas detected in the above-described manner.

That is, the flow rate of the atmospheric gas flowing within the intake pipe 110 or the purge line 115 is determined by a differential pressure between the gas pressure in the interior of the pipe or line and the gas pressure at the inlet of the pipe or line. Since the pressure at the inlet is always constant (atmospheric pressure), the flow rate of the atmospheric gas flowing within the intake pipe 110 or the purge line 115 can be calculated from a pressure value output from the gas concentration/pressure sensor 101.

d) Next will be described general operation of the gas concentration/pressure sensor 101 which operates on the basis of the above-described principle.

As in the gas concentration sensor 1 of the first embodiment, an atmospheric gas flows from the gas inlet port 13 into the measurement chamber 7 and then flows to the outside from the gas outlet port 15. On the basis of the propagation speed of an ultrasonic wave within the measurement chamber 7, the concentration of vaporized fuel in the atmospheric gas is measured.

In particular, in the fourth embodiment, the pressure of the atmospheric gas is measured within the measurement chamber 7. Specifically, an ultrasonic wave transmitted from the ultrasonic element 5 passes through the atmospheric gas within the measurement chamber 7 and is reflected by the reflection surface 9. The reflected wave passes through the atmospheric gas and is received by the same ultrasonic element 5. As will be described below, the drive/calculation circuit 3 subjects the reception wave to integration processing to thereby calculate an integration value of the reception wave. The integration value of the reception wave is a value relating to the pressure of the atmospheric gas, and the drive/calculation circuit 3 obtains the pressure of the atmospheric gas by use of a predetermined map and in accordance with a procedure which will be described in detail later.

Further, the flow rate of the atmospheric gas is calculated from the pressure of the atmospheric gas in accordance with a procedure which will be described in detail below.

e) Next, the procedure for detection of vaporized fuel concentration and atmospheric gas pressure will be described in more detail, together with processing in the drive/calculation circuit 3. It is to be noted that in FIG. 12 the internal structure of a microprocessor 21 is illustrated functionally.

(1) First, the procedure for detection of vaporized fuel concentration will be described.

Figure 12:
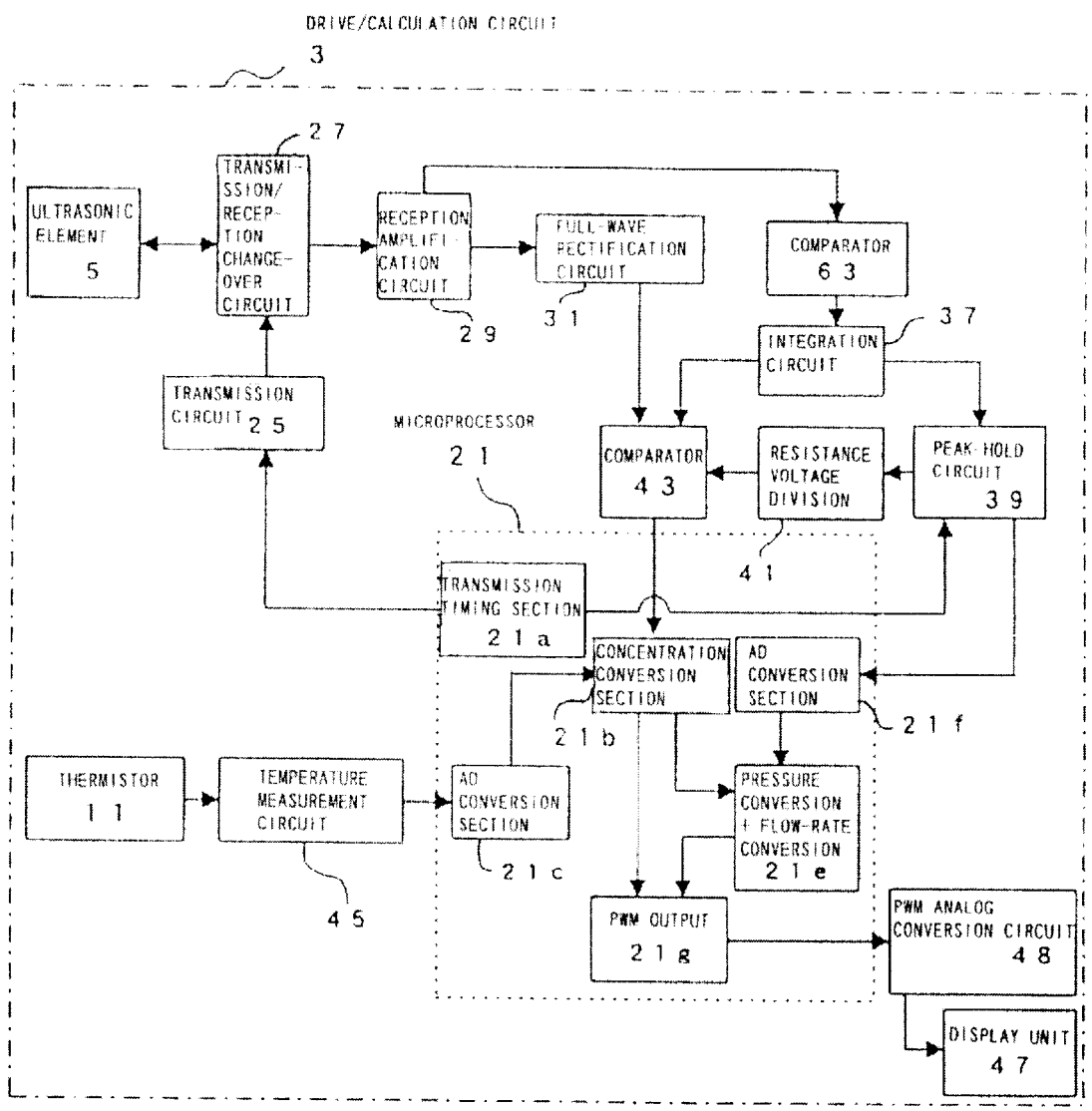
FIG. 12 is a block diagram showing the electrical configuration of the gas concentration/pressure sensor of the fourth embodiment.

As shown in the block diagram of FIG. 12, the transmission timing section 21a of the microprocessor 21 produces a signal indicating a transmission timing, which is sent to the transmission circuit 25. An electrical pulse signal output from the transmission circuit 25 is transmitted to the ultrasonic element 5 via a transmission/reception changeover circuit 27. The ultrasonic element 5 converts the electrical pulse signal to an ultrasonic wave (transmission wave) and transmits it toward the reflection surface 9.

Pulse energy (a reception wave) received by the ultrasonic element 5 after being reflected by the reflection surface 9 is converted to an electrical signal by the ultrasonic element 5.

At this point in time, the transmission/reception changeover circuit 27 switches the signal path from the transmission circuit 25 to a reception amplification circuit 29. Therefore, the electrical signal (indicating the reception wave) from the ultrasonic element 5 is fed to a comparator 63 in which the reception wave is converted to a square wave. The integration circuit 37 integrates the square wave to thereby obtain an integral value, and the peak-hold circuit 39 holds a peak value of the integral value. Subsequently, the resistance-voltage-division circuit 41 sets a value which is equal to a given fraction (e.g., ½) of the peak value and outputs it as a threshold level (reference value) for the comparator 43.

For actual detection of vaporized fuel concentration, after the reception wave is amplified by the reception amplification circuit 29 and subjected to full-wave rectification performed by the full-wave rectification circuit 31, the comparator 43 judges whether an integral value of the reception wave has attained the reference value. When the integral value is judged to have attained the reference level, the comparator 43 transmits to the concentration conversion section 21b of the microprocessor 21 a signal which reports the judgement result.

The time of reception of the signal is a reception timing (arrival time). It is to be noted that the transmission timing (emission time) is transmitted in advance from the transmission timing section 21a to the concentration conversion section 21b and stored therein.

Upon reception of the signal from the comparator 43, the concentration conversion section 21b of the microprocessor 21 calculates the concentration of vaporized fuel from the propagation period in a manner similar to that in the first embodiment, while taking into consideration the temperature conditions.

The thus-obtained concentration of vaporized fuel is converted to a PWM (pulse width modulation) output by a PWM output section 21g, and then to an analog value by a PWM analog conversion circuit 48. The analog value is displayed on, for example, the display unit 47.

(2) Next will be described a procedure for detecting the pressure of the atmospheric gas and calculating the flow rate of the atmospheric gas on the basis of the pressure.

The peak voltage level held in the peak-hold circuit 39 in (1) above is converted to a digital voltage level by an AD conversion section 21f of the microprocessor 21, and the digital voltage level is fed to a pressure conversion/flow-rate conversion section 21e.

In the pressure conversion/flow-rate conversion section 21e, the voltage level is converted to pressure of the atmospheric gas, which is further converted to flow rate of the atmospheric gas.

Specifically, the pressure of the atmospheric gas is detected from the voltage level by use of a map (FIG. 13) showing the relationship between voltage level and atmospheric gas pressure. This map is stored in ROM (not shown) provided in the microprocessor 21 and is retrieved and used when necessary.

Figure 14:
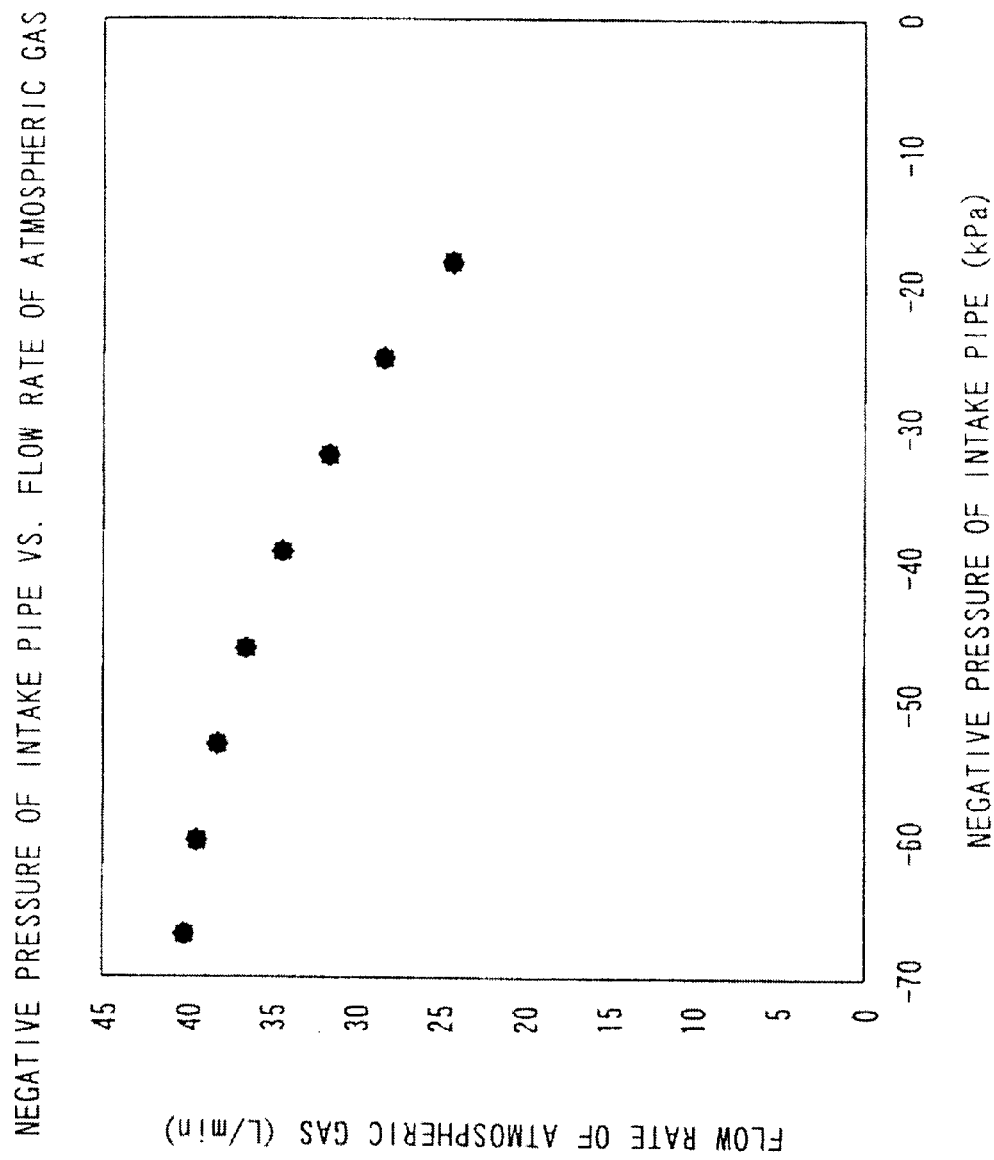
FIG. 14 is a graph relating to the fourth embodiment and showing a map for obtaining gas flow rate.

(3) Subsequently, the flow rate of the atmospheric gas is detected from the pressure of the atmospheric gas detected in the above-described process (2), by use of a map (FIG. 14) showing the relationship between gas pressure within a pipe (the intake pipe 110 or the canister purge line 115) and flow rate of the atmospheric gas flowing therethrough. This map is also stored in ROM (not shown) provided in the microprocessor 21 and is retrieved and used when necessary.

The pressure and flow rate of the atmospheric gas are converted to PWM outputs by the PWM output section 21g and then to analog values by the PWM analog conversion circuit 48. The analog values are then displayed on, for example, the display unit 47.

e) The gas concentration/pressure sensor 101 of the fourth embodiment achieves the following effects.

(1) Since concentration, pressure, and flow rate of a gas can be measured through use of a single gas sensor, cost and installation space of the gas sensor can be reduced as compared with the case in which concentration, pressure, and flow rate of a gas are measured by use of different gas sensors.

(2) As in the gas concentration sensor of the first embodiment, gas concentration can be measured accurately at all times through setting of the reference value in accordance with the pressure of the atmospheric gas.

(3) Stable measurement of gas pressure is possible over a long period, because no mechanically-movable member is necessary.

(4) Since gas flow rate is calculated from the gas pressure, the number of structural elements of the sensor relating to measurement of gas flow rate can be reduced, whereby the sensor can be rendered compact.

d) Next will be described an evaluation test performed in order to confirm the effects of the gas concentration/pressure sensor 101 of the fourth embodiment.

(1) System Used in the Evaluation Test

Figure 11:
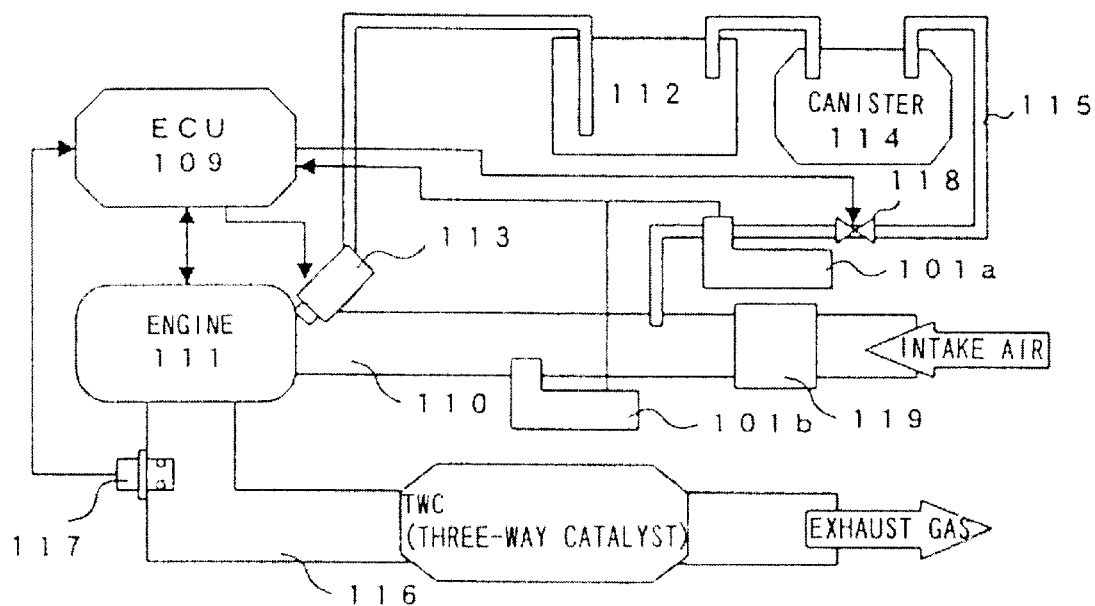
FIG. 11 is an explanatory view showing a fuel supply system of the fourth embodiment.

A system used in the evaluation test has a structure basically the same as that of the system of FIG. 11. However, in place of the canister 114, a gas cylinder is connected to the inlet of the canister purge line 115 in order to supply from the gas cylinder a gas mixture of vaporized fuel and air of known concentration.

A 4-cylinder engine having a displacement of 1800 cc was used.

(2) Test Method

The internal pressure of the canister purge line 115 and the vaporized fuel concentration of the gas supplied to the canister purge line 115 were set to corresponding condition values shown in Table 2. In this state, the vaporized fuel concentration and the pressure and flow rate of the atmospheric gas were measured through use of the gas concentration/pressure sensor 101a disposed at the canister purge line 115.

The internal pressure of the canister purge line 115 was controlled by means of operating conditions of the engine.

Confirmation as to whether the vaporized fuel concentration and the pressure and flow rate of the atmospheric gas were properly set was performed on the basis of values output from an infrared-type concentration analyzer, a diaphragm-type pressure gauge, and a hot-wire-type flow rate sensor, which are attached to the canister purge line 115.

(3) Test Results

Test conditions and test results are shown in Table 2.

TABLE 2

| | Set values | | Measurements of sensor 101a | | |
|---|---|---|---|---|---|
| Time | Purge line pressure | Vaporized fuel concentration of supply gas | Purge line pressure | Vaporized fuel concentration | Flow rate |
| 0–1 | −70 | 0 | −70 | 0 | 40 |
| 1–4 | −70 | 10 | −70 | 10 | 40 |
| 4–7 | −70 | 20 | −70 | 20 | 40 |
| 7–8 | −70 | 0 | −70 | 0 | 40 |
| 8–9 | −40 | 0 | −40 | 0 | 35 |
| 9–12 | −40 | 10 | −40 | 10 | 35 |
| 12–15 | −40 | 20 | −40 | 20 | 35 |
| 15–16 | −40 | 10 | −40 | 10 | 35 |

As shown in Table 2, the gas concentration/pressure sensor 101a indicates concentrations, pressures, and flow rates which are equal to corresponding set values.

Accordingly, it was confirmed that the gas concentration/pressure sensor 101a can accurately measure vaporized fuel concentration, pressure, and flow rate of the atmospheric gas.

In Table 2, the unit for time is minutes; the unit for pressure is KPa; the unit for flow rate is liters/minute; and the unit for vaporized fuel concentration is vol. %.

The present invention is not limited to the above-described embodiment, and may be practiced in various ways without departing from the sprit of the present invention. For example:

(1) In the first through fourth embodiments, two ultrasonic elements may be disposed such that transmission and reception of ultrasonic waves are performed by the respective ultrasonic elements.

(2) In the first through fourth embodiments, a shaped reception wave (i.e., a portion of a reception wave) is used. However, the entirety of the reception wave may be used as is. In view of elimination of noise and simplification of calculation, preferably a portion of a reception wave is integrated.

(3) In the gas concentration/pressure sensor 101 of the fourth embodiment, pressure of an atmospheric gas is calculated from an integral value of an ultrasonic reception wave. Alternatively, a method of detecting the pressure of the atmospheric gas on the basis of a different parameter (e.g., maximum amplitude of an ultrasonic reception wave) may be employed, indicating strength of the reception wave.

(4) The gas concentration/pressure sensor 101 of the fourth embodiment is used as a gas sensor for measuring concentration, pressure, and flow rate of a gas. However, the gas concentration/pressure sensor 101 may be used as a gas sensor for measuring one or two of the above-described quantities of state.

(5) In the fourth embodiment, the gas concentration/pressure sensor 101 is disposed at both the intake pipe 110 and the canister purge line 115. However, a sufficient effect is obtained even when the gas concentration/pressure sensor 101 is disposed at either the intake pipe 110 or the canister purge line 115.

Effects of the Invention (1) As having been described in detail, the ultrasonic-wave propagation time measurement method of (1) to (5) above enables a reference value itself to be adjusted on the basis of an integral value of a reception wave or a portion thereof and in consideration of influence of gas pressure and the like. Therefore, during actual measurement, propagation time can be measured accurately even when the reception wave is attenuated due to gas pressure or any other cause.

(2) Since the gas sensor of (6) above can accurately measure propagation time in accordance with the above-described ultrasonic-wave propagation-time measurement method, gas concentration can be accurately detected at all times.

(3) Since the gas sensor of (10) above measures gas pressure on the basis of an integral value of a reception wave or a portion thereof, no mechanically-movable member is required, so that stable measurement can be performed over a long period of time.

(4) The gas sensor of (11) achieves effects similar to those achieved by the gas sensors mentioned in (2) and (3) above. In addition, since both gas concentration and gas pressure can be measured by use of a single gas sensor, the cost and installation space of the gas sensor can be decreased as compared with the case in which gas concentration and gas pressure are measured by use of different gas sensors.

(5) The gas sensor of (12) calculates gas flow rate from gas pressure, which is measured in a manner similar to that used for the gas sensor described in (3) above. Therefore, the gas sensor (12) can measure both gas pressure and gas flow rate, although its basic structure is the same as that of the gas sensor described in (3) above. Accordingly, when the gas sensor (12) is used, gas pressure and gas flow rate can be measured through use of a single gas sensor, and the cost and installation space of the gas sensor can be decreased as compared with the case in which gas pressure and gas flow rate are measured by use of different gas sensors.

(6) The gas sensor (13) achieves effects similar to those achieved by the gas sensors mentioned in (2), (3), and (4) above. In addition, when the gas sensor (13) is used, gas concentration, gas pressure, and gas flow rate can be measured through use of a single gas sensor, and the cost and installation space of the gas sensor can be decreased as compared with the case in which gas concentration, gas pressure, and gas flow rate are measured by use of different gas sensors.

This application is based on Japanese Patent Application Nos. Hei. 11-229776 filed Aug. 16, 1999 and 2000–186379 filed Jun. 21, 2000, which are incorporated herein by reference in their entirety.

What is claimed is:

1. A method for measuring ultrasonic propagation time comprising the steps of:

providing a flowing gas;

transmitting into the flowing gas an ultrasonic transmission wave by an ultrasonic element at a selected transmission time;

receiving as a reception wave by the same ultrasonic element or a different ultrasonic element a reflection wave of the ultrasonic transmission wave;

rectifying the reception wave to form a rectified wave;

integrating the rectified wave to obtain an integral value of the reception wave; and determining the ultrasonic propagation time as a period of time between the transmission time and a time when the integrated value attains a threshold level, wherein the threshold level is set based on the integral value of the reception wave.

2. The method for measuring ultrasonic propagation time as claimed in claim 1, which comprises determining the ultrasonic propagation time as a period of time between the transmission time and a time when the integrated value attains a threshold level, wherein the threshold level is set at one half of the maximum of the integral value of the reception wave.

3. The method for measuring ultrasonic propagation time as claimed in claim 1, which comprises providing a flowing gas within an intake pipe or canister purge line in an internal combustion engine.

4. A method for determining a concentration, a velocity, or a pressure of a flowing gas, the method comprising the steps of:

providing a flowing gas;

measuring an ultrasonic propagation time in the flowing gas as claimed in claim 1; and determining the concentration, the velocity, or the pressure of the flowing gas based upon the ultrasonic propagation time and the temperature of the gas.

5. The method for determining a concentration, a velocity, or a pressure of a flowing gas as claimed in claim 4, wherein the step of providing a flowing gas comprises the step of providing a fuel within an intake pipe or canister purge line in an internal combustion engine; and wherein the step of determining the concentration, the velocity, or the pressure of the flowing gas comprises the step of determining a concentration, a velocity, or a pressure of the fuel based upon the ultrasonic propagation time and the temperature of the gas.

6. A gas sensor for detecting concentration, velocity, or pressure of a flowing gas into which an ultrasonic transmission wave is transmitted by an ultrasonic element at a selected transmission time, and a reflection wave of the ultrasonic transmission wave is received as a reception wave by the same ultrasonic element or a different ultrasonic element, the gas sensor comprising:

means for rectifying the reception wave to form a rectified wave;

means for integrating the rectified wave to obtain an integral value of the reception wave;

means for determining the ultrasonic propagation time as a period of time between the transmission time and a time when the integrated value attains a threshold level, wherein the threshold level is set based on the integral value of the reception wave; and means for determining a concentration, a velocity, or a pressure of the flowing gas based upon the ultrasonic propagation time and the temperature of the gas.

* * * * *